US005484606A

United States Patent [19]

Dhabhar

[11] Patent Number: 5,484,606
[45] Date of Patent: Jan. 16, 1996

[54] PROCESS FOR REDUCING THE PRECIPITATION OF DIFFICULTY SOLUBLE PHARMACEUTICAL ACTIVES

[75] Inventor: Dadi J. Dhabhar, Cincinnati, Ohio

[73] Assignee: The Procter & Gamble Company, Cincinnati, Ohio

[21] Appl. No.: 185,652

[22] Filed: Jan. 24, 1994

[51] Int. Cl.$^6$ .............................. A61K 9/48; A61K 9/10; A61K 31/79

[52] U.S. Cl. ........................ 424/455; 424/452; 514/772.2; 514/772.4; 514/772.5; 514/937; 514/962

[58] Field of Search ................................. 514/962, 937, 514/772.2, 772.5; 424/452, 455

[56] References Cited

U.S. PATENT DOCUMENTS

| | | |
|---|---|---|
| 3,528,179 | 9/1970 | Smith ............................... 34/1 |
| 3,851,051 | 11/1974 | Miskel et al. .................... 424/37 |
| 4,015,341 | 4/1977 | McKinney et al. ............... 34/4 |
| 4,067,960 | 1/1978 | Fadda ............................... 424/14 |
| 4,198,391 | 4/1980 | Grainger .......................... 424/37 |
| 4,294,624 | 10/1981 | Veltman ........................... 127/62 |
| 4,418,083 | 11/1983 | McKinney et al. ............. 426/242 |
| 4,664,924 | 5/1987 | Sugisawa et al. ............... 426/242 |
| 4,690,823 | 9/1987 | Lohner et al. .................. 424/456 |
| 4,720,924 | 1/1988 | Hradecky et al. ............... 34/1 |
| 4,744,988 | 5/1988 | Brox ................................ 424/456 |
| 4,780,316 | 10/1988 | Brox ................................ 424/456 |
| 4,816,270 | 3/1989 | Turner ............................ 426/243 |
| 4,820,364 | 4/1989 | Graham ........................... 156/69 |
| 4,857,312 | 8/1989 | Hegasy et al. ................... 424/80 |
| 4,888,239 | 12/1989 | Brox ................................ 428/402.2 |
| 4,968,509 | 11/1990 | Radebaugh et al. ............. 424/470 |
| 5,001,844 | 3/1991 | Lhonneur et al. ................ 34/1 |
| 5,006,595 | 4/1991 | Smith et al. ..................... 524/548 |
| 5,091,200 | 2/1992 | Kang et al. ...................... 426/24 |
| 5,141,961 | 8/1992 | Coapman ........................ 514/629 |

FOREIGN PATENT DOCUMENTS

| | | | |
|---|---|---|---|
| 132480 | 2/1985 | European Pat. Off. ............ | A61J 3/00 |
| 60-92214 | 5/1985 | Japan . | |
| 61-63614 | 4/1986 | Japan . | |
| 3-5418 | 1/1991 | Japan . | |
| 2185887 | 8/1987 | United Kingdom ............ | A61K 31/55 |
| 2209114 | 5/1989 | United Kingdom ............ | A23L 3/40 |
| WO95/04527 | 2/1995 | WIPO .......................... | A61K 31/165 |

OTHER PUBLICATIONS

D. Q. M. Craig, "Polyethylene Glycols and Drug Release", Drug Dev. and Industrial Pharmacy, 16(17), pp. 2501–2526 (1990).

J. E. Hilton et al., "The Effect of Wetting Agents on the Dissolution of Indomethacin Solid Dispersion Systems", Int. J of Pharm, 31 pp. 157–164, (1986).

L. Lachman et al., "Soft Gelatin Capsules", The Theory and Practice of Industrial Pharmacy, (Lea & Febiger, Phil.) pp. 398–412 (1986).

H. Seager, "Soft Gelatin Capsules: A Solution to Many Tableting Problems", Pharmaceutical Technology, Sep. 1985.

R. P. Scherer Technical Data Bulletin, "Scherersol™ The Best Solution for Better Drug Absorption".

CA98(8):59913b Oct. 16, 1982 Japan.

Ogawa et al. CA. 115:57200n (1991) of JPN 03.005418 (Jan. 11, 1991) (10 pp.).

S.S. Pharm. CA. 103: 129066a (1985) of JPN 60 092214 (May 23, 1985) (4 pp.).

Nosawa CA. 105: 30083h (1986) of JPN 61 06314 (Apr. 1, 1986) (16 pp.).

Ogawa CA. 115: 57200n (1991) of JPN 03005 418 (Jan. 11, 1991).

*Primary Examiner*—Shep Rose
*Attorney, Agent, or Firm*—David K. Dabbiere; Douglas C. Mohl; Jacobus C. Rasser

[57] ABSTRACT

A process for reducing precipitation of difficultly soluble pharmaceutical active in a mixture of polyethylene glycol, polyvinylpyrrolidone and propylene glycol.

20 Claims, No Drawings

PROCESS FOR REDUCING THE PRECIPITATION OF DIFFICULTY SOLUBLE PHARMACEUTICAL ACTIVES

TECHNICAL FIELD

The present invention relates to a process for reducing precipitation of difficultly soluble pharmaceutical actives alone or in combination with additional pharmaceutical actives in a mixture of polyethylene glycol, polyvinylpyrrolidone and propylene glycol.

BACKGROUND OF THE INVENTION

Liquid, and especially concentrated liquid pharmaceutical compositions offer several advantages over solid compositions. Liquids are easy to swallow and provide an excellent vehicle for the uniform delivery of pharmaceutical actives. Moreover, liquids provide a rapid onset of pharmacologic action, since the composition does not first have to disintegrate and dissolve in the gastrointestinal tract. Likewise, concentrated liquid compositions offer certain distinct advantages. These compositions are ideally suited for incorporation into easy-to-swallow soft, flexible capsules. Encapsulation of this nature permits the accurate and uniform delivery of unit dose amounts of a pharmaceutical active, encompassing even those instances where relatively small amounts of a pharmaceutical active are to be delivered. In addition, soft gelatin capsules are aesthetically appealing (especially when filled with a transparent liquid) and can be manufactured in a wide variety of sizes, shapes, and colors.

These advantages notwithstanding, it is, however, often difficult to prepare such compositions using the desired pharmaceutical active. Many pharmaceutical actives are poorly soluble and, therefore, require relatively large volumes of solvent for dissolution, resulting in impractically large doses. Also, encapsulating such large volumes into easy-to-swallow gelatin capsules presents obvious difficulties, suggesting the immediate importance of concentrated liquid compositions. Furthermore, the situation becomes even more complicated when multiple pharmaceutical actives are involved, and particularly where the difficultly soluble pharmaceutical active is in combination with a water soluble pharmaceutical active(s).

The current approach to this solubility problem is to force solubility into small volumes of solvent by means of a step-wise process incorporating intense heat. This step-wise process consists of dissolving the difficultly soluble pharmaceutical active in polyethylene glycol with heat, followed by the addition of any additional pharmaceutical actives. As a separate admixture, polyvinylpyrrolidone is dissolved in a solution of water and propylene glycol. Finally, the polyvinylpyrrolidone solution is then added to the original batch solution to complete the process. While this process has proved to be quite useful in enhancing the solubility of difficultly soluble pharmaceutical actives, there is still a need to improve the stability of the resultant liquid composition. Because the resultant concentrated liquid (or fill) is a supersaturated solution of the difficultly soluble pharmaceutical active, there is a tendency for the dissolved difficultly soluble active to precipitate out of solution.

The present inventor has unexpectedly discovered that by simply changing the order in which certain components are added under the current process, a new composition results having improved stability.

It is, therefore, an object of the present invention to describe a process which provides decreased precipitation of the difficultly soluble pharmaceutical active(s), thus improving the resultant composition's stability. These and other objects of this invention will become apparent in light of the following discussion.

SUMMARY OF THE INVENTION

The present invention relates to a process for reducing precipitation of difficultly soluble pharmaceutical actives in combination with an aqueous phase in a concentrated form, comprising the steps of:

a) combining and mixing until dissolved from about 1% to about 40% of at least one difficultly soluble pharmaceutical active in a solution comprising:
  i) from about 20% to about 70% of a polyethylene glycol;
  ii) from about 1% to about 20% of a polyvinylpyrrolidone; and
  iii) from about 1% to about 10% of a propylene glycol.

The process preferably further comprises combining and mixing until dissolved the above solution with a separate admixture of from about 0.5% to about 20% of at least one additional pharmaceutical active in from about 1% to about 50% of an aqueous phase.

All percentages and ratios used herein are by weight and all measurements are at 25° C., unless otherwise indicated.

DETAILED DESCRIPTION OF THE INVENTION

The term "difficultly soluble pharmaceutical active", as used herein, describes an active having a solubility of less than or equal to 1% by weight in water at 25° C. This term is defined to also include the descriptive terms "sparingly soluble"; "slightly soluble"; "very slightly soluble"; "practically insoluble, or insoluble"; and their equivalents as defined in the USP XXII, p.8 (1990), this reference being incorporated herein by reference in its entirety.

Concentrated Liquid Pharmaceutical Compositions

The highly concentrated liquid pharmaceutical compositions of the present invention comprise the following essential, as well as optional, components.

Polyethylene Glycol

An essential component of the present compositions is a polyethylene glycol. Polyethylene glycols generally are clear, viscous liquids or white solids which are soluble in water and many organic solvents. These polymers correspond to the general formula:

where n is greater than or equal to 4. Polyethylene glycols are described in G. M. Powell, III in Handbook of Water-Soluble Gums & Resins, R. L. Davidson, Ed. (McGraw-Hill, New York, 1980) pp. 18/1–18/31, this reference being incorporated herein by reference in its entirety. Polyethylene glycols, which are also known as "PEGs" or "polyoxyethylenes", are designated by both their average molecular weight range and their average "n" value as in the above designated formula. For example, polyethylene glycol 400, which is also known by the CTFA designation, PEG-8, has an average molecular weight range from 380–420 and an average value of n between 8.2 and 9.1. See *CTFA Cosmetic Ingredient Dictionary*, Third Edition (1982), pp. 201–203; and *The Merck Index*, Tenth Edition, entry 7441, p. 1092

(1983); these two references being incorporated herein by reference in their entirety.

The polyethylene glycols useful herein are mixtures of those which are liquids at room temperature or have a melting point slightly thereabove. Preferred mixtures include those polyethylene glycols having a molecular weight range of from about 300 to about 1000 and corresponding n values of from about 6 to about 20. More preferred are those of polyethylene glycols having a molecular weight range of from about 400 to about 1000 and corresponding n values of from about 8 to about 20. Most preferred are those polyethylene glycols having a molecular weight range of from about 600 to about 1000 and corresponding n values from about 12 to about 20. Liquid and low-melting polyethylene glycols are commercially available from Union Carbide (Danbury, Conn.) under the Carbowax® trademark. See "Carbowax® Polyethylene Glycols", Union Carbide Technical Bulletin f-4772M-ICD 11/86-20M, this reference being incorporated herein by reference in its entirety.

Polyethylene glycols having an average molecular weight below about 300 are not desirable for use in the instant invention since such polyethylene glycols tend to diffuse into, plasticize, and ultimately disrupt the soft gelatin shells which can be employed to encapsulate the compositions described herein.

The process for preparing the highly concentrated liquid compositions of the present invention comprises adding from about 20% to about 70% polyethylene glycol, more preferably from about 35% to about 65%, and most preferably from about 40% to about 60%.

Polyvinylpyrrolidone

An essential component of the present compositions is polyvinylpyrrolidone ("PVP"), which is a polymer of N-vinyl-2-pyrrolidone having the following formula:

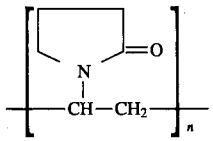

Polyvinylpyrrolidones are described in L. Blecher et al. in *Handbook of Water-Soluble Gums & Resins*, R. L. Davidson, Ed. (McGraw-Hill, New York, 1980) pp. 21/1–21/21, this reference being incorporated herein by reference in its entirety. Polyvinylpyrrolidone has different solubility characteristics based on its polymeric structure. Long-chain polyvinylpyrrolidone, which is also known as povidone, has good solubility in water and a number of organic solvents. Cross-linked polyvinylpyrrolidone, which is also known as crospovidone, is insoluble in virtually all common solvents. Both the soluble and insoluble forms of polyvinylpyrrolidone are commercially available from GAF Chemicals Company (Wayne, N.J.) under the Plasdone® and Polyplasdone® trademarks, respectively, and from BASF Aktiengesellschaft (Ludwigshafen, Germany) under the Kollidon® trademark. Soluble forms of polyvinylpyrrolidone include Plasdone® K-25, Plasdone® K-26/28, Plasdone® K-29/32, Plasdone® C-15, Plasdone® C-30, Plasdone® C-90, Kollidon® 12 PF, Kollidon® 17 PF, Kollidon® 25, Kollidon® 30, and Kollidon® 90. Insoluble forms of polyvinylpyrrolidone include Polyplasdone XL®, Polyplasdone XL®10, Kollidon® CL, and Kollidon® CL-M. See "Tableting With Plasdone®", GAF Technical Bulletin 2302-110RI (1986); "Polyplasdone XL®, Polyplasdone XL®10", GAF Technical Bulletin 2302-099 R2 (1984); and "Kollidon® Grades, Polyvinylpyrrolidone for the Pharmaceutical Industry", BASF Technical Bulletin MEF 129e, Register 2, May 1986 (Bn); these references being incorporated herein by reference in their entirety.

The soluble forms of polyvinylpyrrolidone are preferred for use in the present invention. Preferred are soluble polyvinyl-pyrrolidones having an average molecular weight in the range of from about 8000 to about 630,000; more preferred are those having an average molecular weight in the range of from about 8000 to about 38,000; and most preferred are those having an average molecular weight of about 38,000. Moreover, mixtures of two or more soluble polyvinylpyrrolidones of different average molecular weight can be employed.

The process for preparing the highly concentrated liquid compositions of the instant invention comprises adding from about 1% to about 28% of a soluble polyvinylpyrrolidone, more preferably from about 1% to about 10%, and most preferably from about 1% to about 5%.

Preferably, the ratio of the total amount of polyethylene glycol to polyvinylpyrrolidone should be at least about 2.5:1.

Propylene Glycol

Propylene glycol, which is represented by the formula:

$$CH_3CHOHCH_2OH$$

is well known in the art for its solvent and/or humectant properties. A colorless and viscous liquid, propylene glycol is miscible with water, alcohols and many organic solvents. Propylene glycol is described in *Hawley's Condensed Chemical Dictionary*, pp. 970–971, (Revised by Richard J. Lewis, Sr.) (12th ed. 1993, herein incorporated by reference. Propylene glycol suitable for use in the present invention is obtainable from any number of suppliers, Dow Chemical being one.

Difficulty Soluble Pharmaceutical Actives

The compositions of the instant invention contain at least one difficultly soluble pharmaceutical active as an essential component. In general, these actives have a solubility less than or equal to about 1 percent by weight in water at 25° C. Useful classes of pharmaceutically-active compounds which can be incorporated into the present compositions include analgesics, anti-inflammatory agents, anti-pyretics, calcium channel blockers, beta-blockers, antibacterials, antidepressants, antidiabetics, anti-emetics, antihistamines, cerebral stimulants, sedatives, anti-parasitics, expectorants, diuretics, decongestants, antitussives, muscle relaxants, anti-Parkinsonian agents, bronchodilators, cardiotonics, antibiotics, antivirals, nutritional supplements (such as vitamins, minerals, fatty acids, amino acids, and the like), and mixtures thereof. Difficultly soluble pharmaceutical actives selected from the non-narcotic analgesics/nonsteroidal anti-inflammatory drugs are especially useful in the present invention. Examples of such drugs are disclosed in U.S. Pat. No. 4,522,828, to Sunshine et al., issued Jun. 11, 1985; this patent being incorporated herein by reference in its entirety.

Examples of preferred difficultly soluble pharmaceutical actives useful in the present invention include, but are not limited to, acetaminophen, acetylsalicylic acid, ibuprofen, fenbuprofen, fenoprofert, flurbiprofen, indomethacin, ketoprofen, naproxen, their pharmaceutically-acceptable salts, and mixtures thereof. Acetaminophen is especially preferred for use in the present invention.

The process for preparing the highly concentrated liquid compositions of the instant invention comprises adding from about 1% to about 40% of a difficultly soluble pharmaceutical active, more preferably from about 15% to about 35%, and most preferably from about 20% to about 30%.

Additional Pharmaceutical Actives

The compositions of the instant invention can optionally contain one or more additional pharmaceutical actives having a solubility greater than the difficultly soluble pharmaceutical actives described above. In general, these actives have a solubility greater than about 1 percent by weight in water at 25° C. Such additional pharmaceutical actives may also be selected from among the pharmaceutical categories previously mentioned.

Specific examples of additional pharmaceutical actives useful in the present invention include, but are not limited to, pseudoephedrine and its salts such as pseudoephedrine hydrochloride; dextromethorphan and its salts such as dextromethorphan hydrobromide; doxylamine and its salts such as doxylamine succinate; phenindamine and its salts such as phenindamine hydrogen tartrate; pheniramine and its salts such as pheniramine maleate; chlorpheniramine and its salts such as chlorpheniramine maleate; ephedrine and its salts such as ephedrine sulfate; triprolidine and its salts such as triprolidine hydrochloride; diphenhydramine and it salts such as diphenhydramine hydrochloride, diphenhydramine citrate, and diphenhydramine 8-chlorotheophyllinate; phenyltoxylamine and its salts; guaifenesin; phenylpropanolamine hydrochloride; and mixtures thereof. Preferred additional pharmaceutical actives are dextromethorphan hydrobromide, doxylamine succinate, pseudoephedrine hydrochloride, chlorpheniramine maleate, guaifenesin, triprolidine hydrochloride, diphenhydramine hydrochloride and mixtures thereof.

A further class of optional actives include those useful in promoting or maintaining healthy skin. Examples of such actives are disclosed in U.S. Pat. No. 5,073,371, to Turner et al., issued Dec. 17, 1991, this patent being incorporated herein by reference in its entirety.

The process for preparing the highly concentrated liquid compositions of the instant invention comprises adding one or more of these optionally additional pharmaceutical actives at a concentration of from about 0.5% to about 20%.

Coolants

In addition, the present invention may optionally incorporate a cooling agent or a combination of cooling agents. Suitable cooling agents are those described in U.S. Pat. No. 4,136,163, Jan. 23, 1979, to Watson et al., U.S. Pat. No. 4,230,668, Oct. 28, 1980, to Rowsell et al. and U.S. Pat. No. 4,032,661, to Rowsell et al., all of which are herein incorporated by reference. A particularly preferred cooling agent is N-ethyl-p-menthane-3-carboxamide (WS-3 supplied by Sterling Organics), taught by the above incorporated U.S. Pat. No. 4,136,163. Another particularly preferred cooling agent is 3-1-menthoxypropane 1,2-diol (TK-10 supplied by Takasago Perfumery Co., Ltd., Tokyo, Japan). This material is described in detail in U.S. Pat. No. 4,459,425, Jul. 10, 1984 to Amano et al. and incorporated herein by reference.

Other Optional Components

Optional components which can be incorporated into the compositions of the instant invention include colorings, flavorings, preservatives, lubricants, flow-enhancers, filling aids, anti-oxidants, essences, and other aesthetically pleasing components.

Process for Solubilizing Difficultly Soluble Pharmaceutical Actives

The highly concentrated liquid pharmaceutical compositions are prepared using art-recognized principles and methodologies in mixing the ingredients together and in choosing the type of mixing equipment to be used. In a preferred manner of execution, the difficultly soluble pharmaceutical active, polyethylene glycol, propylene glycol and polyvinylpyrrolidone, are combined in the presence of heat and mixed until dissolved to form a homogeneous solution. Upon dissolution of the difficultly soluble pharmaceutical active, any additional pharmaceutical actives may then be added to this batch solution or dissolved separately in an aqueous phase. These two solutions are then combined.

Soft Gelatin Capsules

Preselected amounts of the concentrated liquid pharmaceutical compositions of the present invention can also be encapsulated in a soft gelatin shell. Optionally, the soft gelatin shell is essentially transparent so as to enhance the aesthetic qualities of the capsule. The soft gelatin shells comprise the following essential, as well as optional, components.

Gelatin

Gelatin is an essential component of the soft gelatin shells of the instant invention. The starting gelatin material used in the manufacture of soft capsules is obtained by the partial hydrolysis of collagenous material, such as the skin, white connective tissues, or bones of animals. Gelatin material can be classified as Type A gelatin, which is obtained from the acid-processing of porcine skins and exhibits an isoelectric point between pH 7 and pH 9; and Type B gelatin, which is obtained from the alkaline-processing of bone and animal (bovine) skins and exhibits an isoelectric point between pH 4.7 and pH 5.2. Blends of Type A and Type B gelatins can be used to obtain a gelatin with the requisite viscosity and bloom strength characteristics for capsule manufacture. Gelatin suitable for capsule manufacture is commercially available from the Sigma Chemical Company, St. Louis, Mo. For a general description of gelatin and gelatin-based capsules, see *Remingtons' Pharmaceutical Sciences*, 16th ed., Mack Publishing Company, Easton, Pa. (1980), page 1245 and pages 1576–1582; and U.S. Pat. No. 4,935,243, to Borkan et al., issued Jun. 19, 1990; these two references being incorporated herein by reference in their entirety.

The soft gelatin shell of the capsules of the instant invention, as initially prepared, comprises from about 20% to about 60% gelatin, more preferably from about 25% to about 50% gelatin, and most preferably from about 40% to about 50% gelatin. The gelatin can be of Type A, Type B, or a mixture thereof with bloom numbers ranging from about 60 to about 300.

Plasticizer

A plasticizer is another essential component of the soft gelatin shells of the instant invention. One or more plasticizers is incorporated to produce a soft gelatin shell. The soft gelatin thus obtained has the required flexibility characteristics for use as an encapsulation agent. Useful plasticizers of the present invention include glycerin, sorbitan, sorbitol, or similar low molecular weight polyols, and mixtures thereof.

The shell of the present invention, as initially prepared, comprises from about 10% to about 35% plasticizer, preferably from about 10% to about 25% plasticizer, and most preferably from about 10% to about 20% plasticizer. A preferred plasticizer useful in the present invention is glycerin.

Water

The soft gelatin shells of the instant invention also comprise water as an essential component. Without being limited by theory, the water is believed to aid in the rapid dissolution or rupture of the soft gelatin shell upon contact with the gastrointestinal fluids encountered in the body.

The shell of the present invention, as initially prepared, comprises from about 15% to about 50% water, more preferably from about 25% to about 40% water, and most preferably from about 30% to about 40% water.

Other Optional Components

Other optional components which can be incorporated into the soft gelatin shells include colorings, flavorings, preservatives, anti-oxidants, essences, and other aesthetically pleasing components.

Soft Gelatin Shell Preparation and Encapsulation

The solubilized pharmaceutical compositions of the present invention can be encapsulated within any conventional soft gelatin shell that is capable of substantially containing the composition for a reasonable period of time. The soft gelatin shells of the instant invention can be prepared by combining appropriate amounts of gelatin, water, plasticizer, and any optional components in a suitable vessel and agitating and/or stirring while heating to about 65° C. until a uniform solution is obtained. This soft gelatin shell preparation can then be used for encapsulating the desired quantity of the solubilized fill composition employing standard encapsulation methodology to produce one-piece, hermetically-sealed, soft gelatin capsules. The gelatin capsules are formed into the desired shape and size so that they can be readily swallowed. The soft gelatin capsules of the instant invention are of a suitable size for easy swallowing and typically contain from about 100 mg to about 2000 mg of the solubilized pharmaceutical active composition. Soft gelatin capsules and encapsulation methods are described in P. K. Wilkinson et al., "Softgels: Manufacturing Considerations", *Drugs and the Pharmaceutical Sciences*, 41 (Specialized Drug Delivery Systems), P. Tyle, Ed. (Marcel Dekker, Inc., New York, 1990) pp.409–449; F. S. Hom et al., "Capsules, Soft", *Encyclopedia of Pharmaceutical Technology*, vol. 2, J. Swarbrick and J. C. Boylan, eds. (Marcel Dekker, Inc., New York, 1990) pp. 269–284; M. S. Patel et al., "Advances in Softgel Formulation Technology", *Manufacturing Chemist*, vol. 60, no. 7, pp. 26–28 (July 1989); M. S. Patel et al., "Softgel Technology", *Manufacturing Chemist*, vol. 60, no. 8, pp. 47–49 (August 1989); R. F. Jimerson, "Softgel (Soft Gelatin Capsule) Update", *Drug Development and Industrial Pharmacy* (*Interphex '86 Conference*), vol. 12, no. 8 & 9, pp. 1133–1144 (1986); and W. R. Ebert, "Soft Elastic Gelatin Capsules: A Unique Dosage Form", *Pharmaceutical Technology*, vol. 1, no. 5, pp. 44–50 (1977); these references are incorporated by reference herein in their entirety. Methods for tempering soft gelatin capsules are described in U.S. Pat. No. 5,200,191 to Steele et al., herein incorporated by reference. The resulting soft gelatin capsule is soluble in water and in gatrointestinal fluids. Upon swallowing the capsule, the gelatin shell rapidly dissolves or ruptures in the gastrointestinal tract thereby introducing the pharmaceutical actives into the physiological system.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention.

EXAMPLE I

Solubilized Pharmaceutical Composition

A highly concentrated solution containing acetaminophen in combination with other pharmaceutical actives is prepared from the following ingredients:

| Ingredients | Weight % |
| --- | --- |
| Acetaminophen | 27.17 |
| Pseudoephedrine HCl | 3.26 |
| Dextromethorphan HBr | 1.09 |
| Doxylamine Succinate | 0.68 |
| Polyethylene Glycol 600 | 29.76 |
| Polyethylene Glycol 1000 | 27.17 |
| Propylene Glycol | 4.35 |
| Polyvinylpyrrolidone[1] | 2.17 |
| Water Purified | 4.35 |

A solution of the polyethylene glycols, propylene glycol, and polyvinylpyrrolidone is prepared by mixing and warming these components to 70° C. Acetaminophen is then dissolved into this solution stirring and heating the solution to 120° C. in the presence of nitrogen gas. Once the acetaminophen is dissolved, the solution is removed from the heat. In a separate container, pseudoephedrine HCl, dextromethorphan HBr and doxylamine succinate are dissolved in water at room temperature by stirring. Finally, this separate admixture is combined with the original batch solution and mixed until uniform.

Examples II–III are further examples of concentrated solutions containing acetaminophen in combination with other pharmaceutical actives and are manufactured in a manner substantially similar to Example I

EXAMPLE II

| Solubilized Pharmaceutical Composition | |
| --- | --- |
| Ingredients | Weight % |
| Acetaminophen | 27.17 |
| Pseudoephedrine HCl | 3.26 |
| Dextromethorphan HBr | 1.63 |
| Diphenhydramine HCl | 2.72 |
| Polyethylene Glycol 600 | 27.17 |
| Polyethylene Glycol 1000 | 19.17 |
| Glycerin | 8.00 |
| Propylene Glycol | 4.35 |
| Polyvinylpyrrolidone[1] | 2.17 |
| Water Purified | 4.36 |

[1]Available as Kollidon K-30 from BASF Chem.Co. (Viscosity average molecular weight ≈ 38,000)

EXAMPLE III

| Solubilized Pharmaceutical Composition | |
| --- | --- |
| Ingredients | Weight % |
| Acetaminophen | 27.17 |
| Pseudoephedrine HCl | 3.26 |
| Dextromethorphan HBr | 1.08 |
| Chlorpheniramine Maleate | 0.22 |
| Polyethylene Glycol 600 | 29.78 |
| Polyethylene Glycol 1000 | 29.78 |
| Propylene Glycol | 4.35 |
| Polyvinylpyrrollidone[1] | 2.17 |
| Water purified | 2.19 |

[1]Available as Kollidon K-30 from BASF Chem.Co. (Viscosity average molecular weight ≈ 38,000)

EXAMPLE IV

Solubilized Pharmaceutical Composition

A highly concentrated solution containing acetaminophen and guaifenesin in combination with other pharmaceutical actives is prepared from the following ingredients:

| Ingredients | Weight % |
| --- | --- |
| Acetaminophen | 27.17 |
| Pseudoephedrine HCl | 3.26 |
| Dextromethorphan HBr | 1.09 |
| Guaifenesin | 10.87 |
| Polyethylene Glycol 600 | 24.45 |
| Polyethylene Glycol 1000 | 24.45 |
| Propylene glycol | 4.35 |
| Polyvinylpyrrolidone | 2.17 |
| Water Purified | 2.19 |

[1]Available as Kollidon K-30 from BASF Chem.Co. (Viscosity average molecular weight ≈ 38,000)

A solution of polyethylene glycols, propylene glycol, and polyvinylpyrrolidone is prepared by mixing and warming to 70° C. Acetaminophen is then dissolved into this solution, stirring and heating the solution to 120° C. in the presence of nitrogen gas. Once the acetaminophen is dissolved and the solution removed from heat, the guaifenesin is next added and dissolved. In a separate container, pseudoephedrine HCl, dextromethorphan HBr and doxylamine succinate are dissolved in water at room temperature by stirring. Finally, this separate admixture is combined with the original batch solution and mixed until uniform.

EXAMPLE V

Solubilized Pharmaceutical Composition
A highly concentrated solution containing acetaminophen is prepared from the following ingredients

| Ingredients | Weight % |
| --- | --- |
| Acetaminophen | 27.17 |
| Polyethylene Glycol 600 | 32.39 |
| Polyethylene Glycol 1000 | 29.57 |
| Propylene Glycol | 4.35 |
| Polyvinylpyrrolidone[1] | 2.17 |
| Water Purified | 4.35 |

[1]Available as Kollidon K-30 from BASF Chem.Co. (Viscosity average molecular weight ≈ 38,000)

A solution of the polyethylene glycols, propylene glycol, and polyvinylpyrrolidone is prepared by mixing and warming these components to 70° C. Acetaminophen is then dissolved into this solution, stirring and heating the solution to 120° C. in the presence of nitrogen gas. Once the acetaminophen is dissolved, the solution is removed from the heat. Finally, a measured quantity of the aqueous phase is combined with the original batch solution and mixed until uniform.

EXAMPLE VI

Solubilized Pharmaceutical Composition
A highly concentrated solution containing acetaminophen and pseudoephedrine HCl prepared from the following ingredients:

| Ingredients | Weight % |
| --- | --- |
| Acetaminophen | 27.17 |
| Pseudoephedrine HCl | 3.26 |
| Polyethylene Glycol 600 | 30.68 |
| Polyethylene Glycol 1000 | 28.02 |
| Propylene Glycol | 4.35 |
| Polyvinylpyrrolidone[1] | 2.17 |
| Water Purified | 4.35 |

[1]Available as Kollidon K-30 from BASF Chem.Co. (Viscosity average molecular weight ≈ 38,000)

A solution of the polyethylene glycols, propylene glycol, and polyvinylpyrrolidone is prepared by mixing and warming these components to 70° C. Acetaminophen is then dissolved into this solution, stirring and heating the solution to 120° C. in the presence of nitrogen gas. Once the acetaminophen is dissolved, the solution is removed from the heat. In a separate container, pseudoephedrine HCl is dissolved in water at room temperature by stirring. Finally, this separate admixture is combined with the original batch solution and mixed until uniform.

EXAMPLE VII

Softgel Capsule Containing a Solubilized Pharmaceutical Composition
A soft gelatin capsule is first prepared from the following ingredients:

| Ingredients | Weight % |
| --- | --- |
| Gelatin | 47.00 |
| Glycerin | 15.00 |
| Water Purified | qs 100 |

The above ingredients are combined in a suitable vessel and heated with mixing at about 65° C. to form a uniform solution. Using standard encapsulation methodology, the resulting solution is used to prepare soft gelatin capsules containing approximately 920 mg. of the compositions of Examples I–IV. The resulting soft gelatin capsules are suitable for oral administration.

What is claimed is:

1. A process to reduce precipitation of difficulty soluble pharmaceutical actives in combination with an aqueous phase in a concentrated, supersaturated form, comprising the steps of:

a) combining and mixing until dissolved from about 1% to about 40% of at least one difficultly soluble pharmaceutical active in a solution comprising:

i) from about 20% to about 70% of a polyethylene glycol;

ii) from about 1% to about 20% of a polyvinylpyrrolidine; and iii) from about 1% to about 10% of a propylene glycol wherein said solution is heated to a temperature of from about 70° C. to about 120° C. to dissolve said active;

b) removing the solution of step a) from the heat; and c) combining and mixing until uniform the solution from step a) with from about 1% to about 50% of an aqueous phase having from about 0.5% to about 20% of an additional pharmaceutical active.

2. A process according to claim 1 wherein said aqueous phase is water.

3. A process according to claim 2 wherein said difficultly soluble pharmaceutical active is added in an amount from about 15% to about 35%.

4. A process according to claim 3 wherein said difficultly soluble pharmaceutical active is added in an amount from about 20% to about 30%.

5. A process according to claim 4 wherein the ratio of polyethylene glycol to said difficultly soluble pharmaceutical active and said polyvinylpyrrolidine is from about 1:0.3 to about 1:0.8 and from about 1:0.02 to about 1:0.06 respectively.

6. A process according to claim 5 wherein said difficultly soluble pharmaceutical active is selected from the group consisting of acetaminophen, acetylsalicylic acid, ibuprofen, fenbuprofen, fenoprofen, flubiprofen, indomethacin, naproxen, and mixtures thereof.

7. A process according to claim 6 wherein said difficultly soluble pharmaceutical active is acetaminophen.

8. A process according to claim 7 wherein said propylene glycol is added in an amount from about 4% to about 6%.

9. A process according to claim 8 wherein said polyethylene glycol is added in an amount from about 30% to about 65% and said polyvinylpyrrolidone is added in an amount from about 1% to about 10%.

10. A process according to claim 9 wherein said polyethylene glycol is added in an amount from about 40% to about 60% and said polyvinylpyrrolidone is added in an amount from about 1% to about 5%.

11. A process according to claim 10 wherein said polyethylene glycol is selected from a group consisting of PEG-6, PEG-8, PEG-9, PEG-10, PEG-12, PEG-14, PEG-16, PEG-18, PEG-20, and mixtures thereof.

12. A process according to claim 11 wherein said polyethylene glycol is a mixture of PEG-12 and PEG-20.

13. A process according to claim 12 wherein said PEG-12 and PEG-20 are in a ratio of about 1:1.

14. A process according to claim 13 wherein said polyvinylpyrrolidone has an viscosity average molecular weight of about 8,000 to about 38,000.

15. A process according to claim 14 wherein said polyvinylpyrrolidine has an viscosity average molecular weight of about 38,000.

16. A process according to claim 15 wherein said additional pharmaceutical actives are selected from the group of pharmaceutical actives consisting of dextromethorphan, HBr, doxylamine succinate, pseudoephedrine HCl, chlorpheniramine maleate, guaifenesin, triprolidine HCl, diphenhydramine HCl, and mixtures thereof.

17. A process according to claim 16 wherein the said additional pharmaceutical actives are doxylamine succinate, dextromethorphan HBr, and pseudoephedrine HCl.

18. A process according to claim 16 wherein the said additional pharmaceutical actives are dextromethorphan HBr, pseudoephedrine HCl, and guaifenesin.

19. A product made according to the process of claim 1.

20. A product made according to the process of claim 7.

* * * * *